United States Patent
Ideker et al.

(10) Patent No.: US 9,101,779 B2
(45) Date of Patent: Aug. 11, 2015

(54) METHOD AND SYSTEM FOR REDUCING CARDIAC LOW PRESSURE STATES

(75) Inventors: Raymond E. Ideker, Birmingham, AL (US); Gregory Walcott, Wilsonville, AL (US)

(73) Assignee: UAB Research Foundation, Birmingham, AL (US)

( * ) Notice: Subject to any disclaimer, the term of this patent is extended or adjusted under 35 U.S.C. 154(b) by 1485 days.

(21) Appl. No.: 11/874,284

(22) Filed: Oct. 18, 2007

(65) Prior Publication Data

US 2008/0097535 A1 Apr. 24, 2008

Related U.S. Application Data

(60) Provisional application No. 60/852,765, filed on Oct. 19, 2006.

(51) Int. Cl.
*A61N 1/39* (2006.01)

(52) U.S. Cl.
CPC .................... *A61N 1/3925* (2013.01)

(58) Field of Classification Search
USPC .................................... 607/5–6, 14
See application file for complete search history.

(56) References Cited

U.S. PATENT DOCUMENTS

| | | | |
|---|---|---|---|
| 4,424,806 A * | 1/1984 | Newman et al. ............... 601/41 |
| 5,405,362 A * | 4/1995 | Kramer et al. .................. 607/5 |
| 5,733,869 A * | 3/1998 | Burhop et al. ............... 514/13.4 |
| 5,782,879 A * | 7/1998 | Rosborough et al. ............. 607/6 |
| 6,253,108 B1 * | 6/2001 | Rosborough et al. ........... 607/14 |
| 6,259,949 B1 * | 7/2001 | Rosborough et al. ........... 607/14 |
| 6,263,241 B1 * | 7/2001 | Rosborough et al. ............. 607/6 |
| 6,298,267 B1 | 10/2001 | Rosborough et al. |
| 6,556,865 B2 | 4/2003 | Walcott et al. |
| 7,096,064 B2 * | 8/2006 | Deno et al. ......................... 607/9 |
| 2002/0173725 A1 * | 11/2002 | Rock et al. .................... 600/500 |
| 2004/0049117 A1 * | 3/2004 | Ideker et al. .................. 600/510 |
| 2004/0049235 A1 * | 3/2004 | Deno et al. ......................... 607/9 |
| 2004/0162587 A1 * | 8/2004 | Hampton et al. ................. 607/5 |

FOREIGN PATENT DOCUMENTS

WO    WO 00/66222  A1    11/2000

OTHER PUBLICATIONS

Rosborough et al. "Electrical therapy for post defibrillatory pulseless electrical activity." Resuscitation 63 (2004) 65-72.*

* cited by examiner

*Primary Examiner* — Carl H Layno
*Assistant Examiner* — Ankit Tejani
(74) *Attorney, Agent, or Firm* — Myers Bigel Sibley & Sajovec, PA

(57) ABSTRACT

Methods, systems and computer program products are provided for reducing a risk of pulseless electrical activity (PEA) include detecting a first post-defibrillation blood flow of a subject and detecting a second post-defibrillation blood flow of the subject after the first post-defibrillation blood flow. If the first post-defibrillation blood flow of the subject is above a first threshold value and the second post-defibrillation blood flow is below a second threshold value, a plurality of electrical pulses that reduces a risk of PEA is delivered.

27 Claims, 6 Drawing Sheets

METHOD AND SYSTEM FOR REDUCING CARDIAC LOW PRESSURE STATES

RELATED APPLICATIONS

This application claims priority to U.S. Provisional Application Ser. No. 60/852,765, filed Oct. 19, 2006, the disclosure of which is hereby incorporated by reference in its entirety.

FIELD OF THE INVENTION

The present invention concerns methods and systems that may reduce pulseless electrical activity (PEA) following cardiac resuscitation and/or defibrillation.

BACKGROUND OF THE INVENTION

After defibrillation for sudden cardiac arrest defibrillation, many patients remain at risk because their blood pressure and/or pulse is very low or nonexistent post-defibrillation. A low or nonexistent blood pressure and/or pulse with some coordinated ventricular electrical activity is generally referred to as pulseless electrical activity (PEA) or electromechanical dissociation (EMD). When PEA occurs, the prognosis for recovery is very poor and survival rates are low. When left untreated, PEA may be associated with global ischemia and rapidly progressive brain damage. Common courses of treatment include life support measures, such as CPR and the administration of drugs such as epinephrine. However, if cardiac output does not return, PEA is still a significant cause of death post-defibrillation.

U.S. Pat. No. 6,556,865 to Walcott et al. proposes administering a treatment waveform before defibrillation that is insufficient to defibrillate the heart followed by a second treatment waveform that defibrillates the heart and restores organized electrical activity. The first treatment waveform reduces the likelihood of the onset of PEA following the second treatment waveform.

U.S. Pat. No. 6,298,267 to Rosborough et al. proposes an implantable defibrillator that treats PEA after defibrillation by sensing the state of blood flow after defibrillation. If the blood flow is inadequate, the device induces or re-induces ventricular fibrillation and subsequently applies a defibrillation shock to terminate the induced fibrillation.

International Publication No. WO 00/66222 to Rosborough et al. addresses the condition in which cardiac output is not restored after termination of ventricular tachyarrhythmia. Electrical stimulation therapy is applied virtually immediately (i.e., on the order of one minute) after detecting electromechanical disassociation. Once the return of blood flow is detected, the therapy can be stopped.

SUMMARY OF THE INVENTION

According to embodiments of the present invention, methods for reducing a risk of pulseless electrical activity (PEA) include detecting a first post-defibrillation blood flow of a subject and detecting a second post-defibrillation blood flow of the subject after the first post-defibrillation blood flow. If the first post-defibrillation blood flow of the subject is above a first threshold value and the second post-defibrillation blood flow is below a second threshold value, a plurality of electrical pulses that reduces a risk of PEA is delivered.

In some embodiments, systems for reducing a risk of pulseless electrical activity include an electrical pulse generator configured to deliver an electrical pulse to the heart of the subject via one or more electrodes. A controller is configured to control the electrical pulse generator. A detector is configured to detect a first post-defibrillation blood flow of the subject and to detect a second post-defibrillation blood flow of the subject after the first post-defibrillation blood flow. The controller is configured to deliver a plurality of electrical pulses that reduces a risk of PEA if the first post-defibrillation blood flow of the subject is above a first threshold value and the second post-defibrillation blood flow is below a second threshold value.

In some embodiments, methods of reducing a risk of pulseless electrical activity (PEA) include detecting a decrease in blood flow for a heart of a subject post-defibrillation, and delivering a plurality of electrical pulses having a shock profile configured to decrease the risk of pulseless electrical activity and to reduce a likelihood of inducing fibrillation.

In some embodiments, methods of reducing a risk of pulseless electrical activity (PEA) include delivering a defibrillation electrical pulse sufficient to defibrillate a heart of a subject, and detecting a decrease in the blood flow of the subject. If the decrease in the blood flow is detected after a threshold time after defibrillation, a plurality of electrical pulses is administered after the decrease in the blood flow is detected that reduces a risk of pulseless electrical activity.

As will be appreciated by those of skill in the art in light of the present disclosure, the present invention may be embodied as systems, methods and/or computer program products.

DETAILED DESCRIPTION OF EMBODIMENTS OF THE INVENTION

Figure 1:
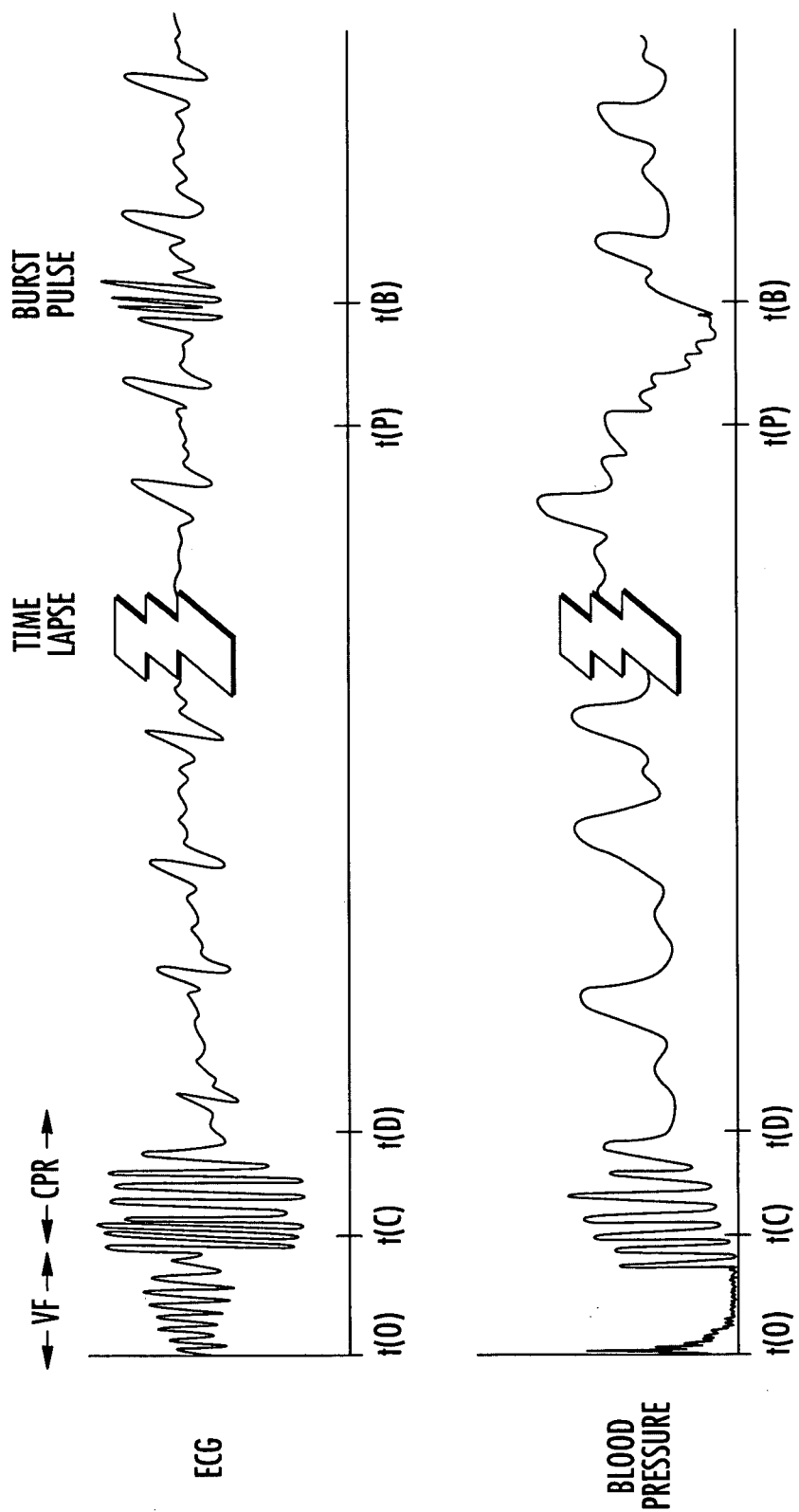
FIG. 1 are graphs of the blood flow and the cardiac signal of as subject according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain regions, components, features or layers may be exaggerated for clarity. Broken lines where used indicate optional features, components or operations.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Like numbers refer to like elements throughout. As used herein the term "comprising" or "comprises" is open-ended, and includes one or more stated elements, steps and/or functions without precluding one or more unstated elements, steps and/or functions. As used herein the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

Embodiments according to the present invention are described with reference to block diagrams and/or operational illustrations of methods, shock generation systems, and computer program products. It is to be understood that each block of the block diagrams and/or operational illustrations, and combinations of blocks in the block diagrams and/or operational illustrations, can be implemented by radio frequency, analog and/or digital hardware, and/or computer program instructions. These computer program instructions may be provided to a processor circuit of a general purpose computer, special purpose computer, ASIC, and/or other programmable data processing apparatus, such that the instructions, which execute via the processor of the computer and/or other programmable data processing apparatus, create means for implementing the functions/acts specified in the block diagrams and/or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used herein, a "shock profile" is the defining characteristics of the shock and may include, for example, parameters relating to a particular electrode configuration, shock vector, peak voltage, the waveform, waveform mean, tilt, polarity, the number of pulses, delays between shocks, the timing of when the shock is given within a cardiac cycle and any other characteristic describing a shock or shock sequence. As used herein, a "shock" having a specified "shock profile" may include one pulse or a plurality of pulses grouped together.

As used herein, the term "burst" pulsing refers generally to electrical cardiac or shock therapy in which a plurality of electrical pulses (i.e., a "burst") are applied to a subject. Burst pulsing can be administered as described herein to decrease the risk for developing PEA. For example, burst pulses may be between 0.5 and 2 ms or between 0.5 and 5 ms in length. The plurality of electrical pulses in a burst can be about 2 to about 6 pulses with a time between pulses of between 5 and 10 ms. A "packet" of burst pulses is a series of bursts that are each separated by an amount of time. The duration of a packet of burst pulses can be between about 1 to about 3 seconds. In some embodiments, the amplitude of the pulses is between 1 and 10 Amps. In some embodiments, a series or packet of bursts are applied, for example, separated by intervals of between 0.5 and 30 seconds. In some embodiments, one burst or two or more bursts separated by a relatively small interval (e.g., about 0.5 to about 3 seconds) can be applied followed by a longer interval (e.g., about 5 to about 60 seconds). This sequence can be repeated. The risk of PEA can be reevaluated during the longer interval using the techniques described herein or subsequent sequences of burst pulses can be delivered automatically. The bursts can be delivered by an implantable defibrillator, and in some embodiments, a relatively longer interval (e.g., about 5 to about 30 seconds) can be used to allow the shocking mechanism of the implantable defibrillator to recharge.

A defibrillation shock is referred to herein as a shock that is configured to defibrillate the heart of a subject, which can include electrical shocks having any suitable shock profile, including biphasic and triphasic shocks or a series of shocks.

Embodiments of the present invention may be used to reduce a risk of and to treat all forms of pulseless electrical activity (PEA), including PEA following ventricular fibrillation, or other cardiac events. In particular, embodiments of the present invention may be used to treat patients remaining at risk for developing PEA despite the return of adequate blood flow post-defibrillation.

FIG. 1 illustrates exemplary graphs of an electrocardiogram (ECG) and blood pressure in a subject. As illustrated, the ECG indicates that the subject is experiencing ventricular fibrillation at time t(0). At time t(C), cardiopulmonary resuscitation (CPR) and/or defibrillation is performed according to known techniques, which can include ventricular defibrillation using shock therapies. At time t(D), the subject's heart has been defibrillated, and a typical, healthy ECG pattern develops. The subject's blood pressure also returns to an adequate level at or shortly after time t(D). The return of the subject's blood pressure to an adequate level (e.g., greater than about 50 mmHg) may be spontaneous or it may be aided by a non-electrical therapy, such as CPR or the administration of drugs such as epinephrine. For example, the adequate level of blood pressure/flow can be above about 50 to 60 mmHg. However, at time t(P), the subject's blood pressure is decreasing, which indicates an increased risk for PEA. The time t(P) can be 5, 10, 20, 30, or 60 or more minutes after CPR is administered at time t(C). When the decrease in blood pressure is detected at time t(P), a burst pulse is subsequently delivered at time t(B), and as a result, the subject's blood pressure is increased. In some embodiments, more than one burst pulse can be delivered.

As shown in FIG. 1, an adequate blood pressure is obtained after defibrillation; however, the blood pressure of the patient is subsequently monitored for a relatively long period of time, such as 10, 20, 30 or 60 or more minutes, after defibrillation and the return of adequate blood pressure. In particular embodiments, one or more non-electrical therapies may be given to the patient to increase blood flow shortly after defibrillation (e.g., at time t(D)). After blood flow has been increased to an adequate level, the patient may still be at risk for a recurrence of PEA; therefore, blood flow can be monitored for a longer period of time. If a subsequent reduction in blood flow occurs, electrical stimulation therapies may be performed.

Without wishing to be bound by theory, it is believed that electrical stimulation therapy may stimulate autonomic nerves to cause sympathetic discharge and an increase in catecholamine levels. However, shortly after defibrillation, the catecholamine levels may be already elevated to extremely high detrimental levels, especially after a long period of fibrillation. Therefore, electrical stimulation therapy may be ineffective if it is administered shortly after defibrillation, e.g., within about five minutes after defibrillation. It is presently believed that electrical stimulation therapy to increase blood flow may be beneficial after the detrimentally high levels of catecholamine has subsided, for example, 10, 20, 30 or 60 or more minutes after defibrillation.

Figure 2:
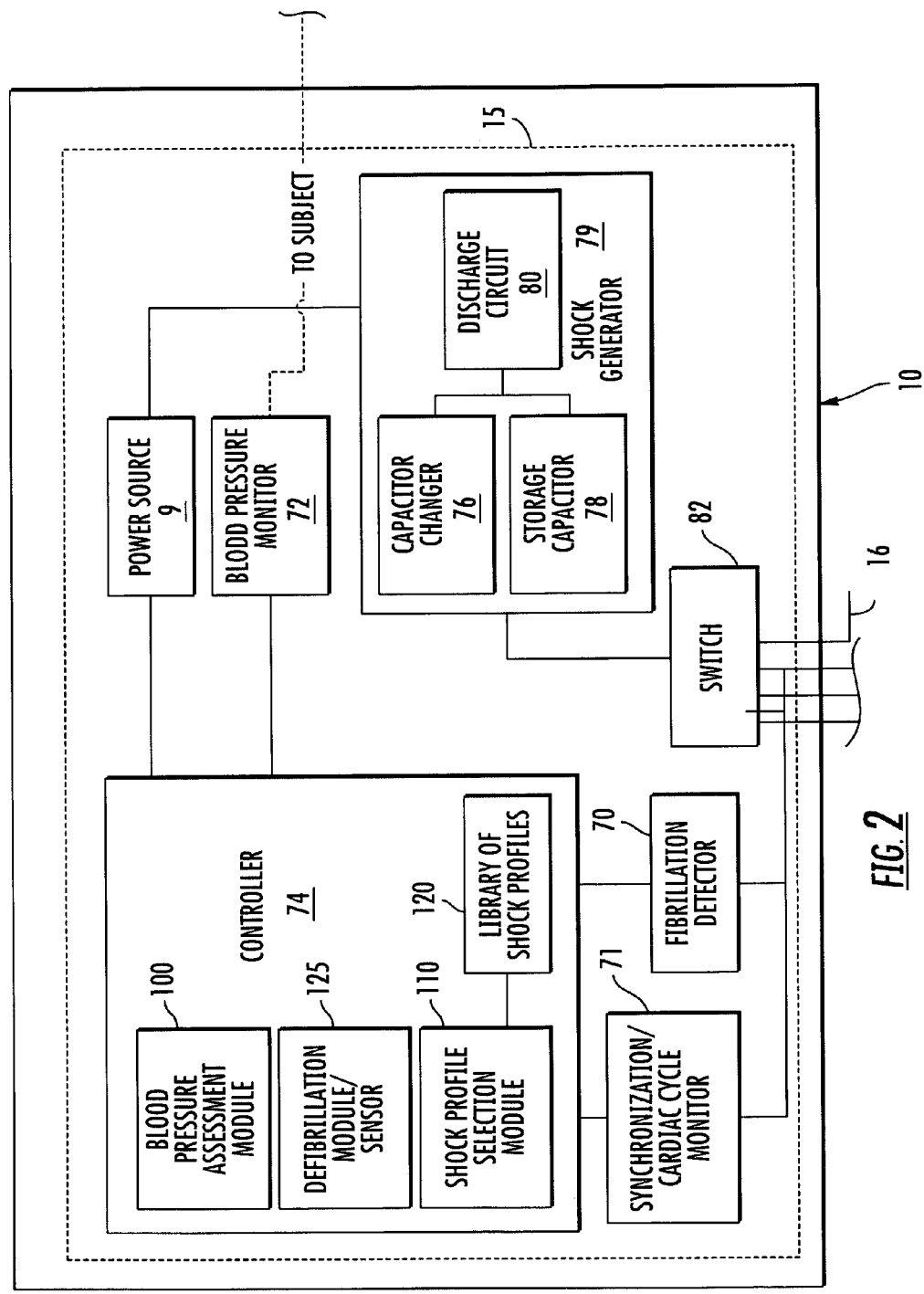
FIG. 2 is a schematic illustration of operational circuitry according to embodiments of the present invention

FIG. 2 illustrates one example of the defibrillator 10 according to embodiments of the invention. The defibrillator 10 includes a housing 13, which contains a power source 9, an electronic circuit 15, a controller 74, and a shock generator 79. The shock generator 79 is operatively associated with the power source 9 and the controller 74 and is configured to deliver different selectable shock profiles. The shock generator includes a capacitor charger 76 and a discharge circuit 80.

The circuit 15 also includes a fibrillation detector 70, a blood pressure monitor 72 and a switch 82. The controller 74 has a blood pressure assessment module/sensor 100, a defibrillation module/sensor 125, a shock profile selection module 110, and a library of shock profiles 120. The shock generator 79 includes a capacitor charger 76, a storage capacitor 78 and a discharge circuit 80. The defibrillator 10 includes leads 16 which can be operatively connected to electrodes (not shown) for defibrillating a patient's heart. The defibrillator 10 can be an internally implantable defibrillator and the housing 13 can be a hermetically sealed housing, or the defibrillator 10 can be an external defibrillator.

In this configuration, the controller 74 controls the delivery of shocks by the shock generator 79 to a subject based on the blood pressure monitor 72 and/or the defibrillation detector 70. In particular, a defibrillation electrical pulse sufficient to defibrillate the heart can be delivered by the shock generator 79 when the fibrillation detector 70 detects fibrillation of the heart. The blood pressure monitor 72 can detect and monitor the blood pressure/flow of the subject. If the blood pressure of the subject returns to a normal amount, e.g., above a threshold amount, followed by a decrease in blood pressure, a plurality of electrical pulses or burst pulse can be delivered after the decrease in the blood pressure is detected. The delivery of the plurality of electrical pulses may reduce the risk of pulseless electrical activity.

The leads 16 and electrodes can be implanted in the patient or the electrodes can be part of an external defibrillation device. The leads 16 and/or electrodes can be configured to deliver a shock profile, such as a defibrillation shock or a burst pulse sequence, to the patient and/or to sense cardiac activity. The blood pressure monitor 72 can also be connected to a hemodynamic sensor (not shown) configured to detect a value that is correlated to blood flow. The circuit 15 can include one or more amplifiers (not shown) for amplifying sensed cardiac and/or hemodynamic signals. Any suitable internal or external hemodynamic sensor can be used that detects a value correlated to blood flow, including impedance sensors, pressure sensors, flow meters, Doppler flow sensors, ion transport sensors, oxygen sensors, pH sensors, piezoelectric sensors, acoustic sensors, and the like.

Electrical cardiac signals are analyzed by the fibrillation detector 70, which determines if ventricular fibrillation (or other types of cardiac arrhythmias, depending on the specific treatment for which the device is configured) is present. The detector 70 may be one of several known to those skilled in the art. It will be appreciated by those of skill in the art that the sensing and/or shocking electrode(s) may also be a plurality of sensing/shocking electrodes with a plurality of signals, such as bipolar configurations, and may also include electrodes that are positioned in alternate cardiac areas as is known in the art, such as, for example, the coronary sinus. The same electrode can be used for sensing cardiac signals and for delivering an electrical current shock profile to the heart, or separate sensing and shocking electrodes can be provided. Electrodes or electrode pairs may be placed in a variety of different locations. A single electrode may participate in more than one electrode pair, so that, for example, two current pathways are achieved through three shocking electrodes. Additional electrodes may be tied together to one member of an electrode pair to provide a single pole, if so desired, and additional electrodes may be provided for following a shock with additional shocks.

Ventricular sensing for timing the shocks for atrial defibrillation may be performed from the RV and/or LV electrodes.

The electronic circuit 15 can also include a synchronization/cardiac cycle monitor 71 for providing synchronization information to the controller 74. The synchronization can be provided by sensing cardiac activity in the right ventricle, but may also include other sensing electrodes which can be combined with the shocking electrodes or employed separately to provide additional assurance that shock pulses (burst pulses and/or defibrillation pulses) are not delivered during sensitive portions of the cardiac cycle so as to reduce the possibility of inducing ventricular fibrillation.

The shocking electrodes may be configured to sense cardiac cycles from electrical signals from the heart, or may have smaller sensing electrodes placed adjacent thereto and thereby provide input to the electronics package as well as provide a predetermined stimulation shock output to predetermined cardiac areas as directed by the controller 74. The electronic circuit 15 may also include a pacing system 130 for reading and monitoring cardiac cycles from the electrical signals from the heart sensed by the electrodes.

Referring to still FIG. 2, in operation, the controller 74 signals the shock generator 79 to generate a shock, which is delivered to the subject via leads 16. In some embodiments, a shock profile is selected by the shock profile selection module 110 from the library of shock profiles 120. For example, the defibrillation module/sensor 125 and/or the blood pressure assessment module 100 can trigger a shock or shock profile based on the signal(s) received from the defibrillation detector 70 and/or the blood pressure monitor 72. The capacitor charging circuit 76 of the shock generator 79 then charges the storage capacitor 78 to a predetermined voltage, typically from the power source 9, which can be a battery source.

The storage capacitor 78 is typically 20 to 400 microfarads in size, and may be a single capacitor or a capacitor network (in addition, separate pulses can be driven by the same or different capacitors). The discharge of the capacitor is controlled by the controller 74 and/or a discharge circuit 80. The controller 74, based on information from the synchronization/cardiac cycle monitor 71, typically allows or directs the preselected shock profile to be relayed to either a discharge circuit 80 for further processing (i.e., to further shape the waveform signal, time the pulse or pulses, etc.) or directly to an output switch such as a switch 82. The controller 74 may also control the desired or proper selection of the predetermined shocking electrode pair(s), where multiple shocking electrodes are used, to direct the switch 82 to electrically activate a desired electrode pair to align the predetermined electric shock pulse pathway through which the shock pulse is provided. As an alternative to a defibrillation detector or blood pressure module, the defibrillation shock profiles may be triggered by an external signal administered by a physician or other medical health professional, with the medical health professional monitoring the patient for the appropriate time of administration. The shock profiles may be preprogrammed into the library of predetermined shock profiles 120 for selection by the shock profile selection module 110. The library of selectable predetermined shock profiles 120 includes specifications and/or instructions that define shocks having various shock profiles. The shock profile is selected by the shock profile selection module 110 and communicated to the discharge circuit 80 for use in processing the shock pulse(s) to the desired shock profile specification. The library of shock profiles 120 can include shock profiles configured to defibrillate a heart and/or shock profiles configured to reduce the risk of PEA post-defibrillation, such as appropriately timed burst pulses.

It will be appreciated by those of skill in the art that the capacitor 78 may be a single capacitor or a bank of parallel capacitors sufficiently charged and sized to be able to provide at least one shock pulse to predetermined electrodes positioned in the heart. Additionally, the capacitor 78 can be two or more separately charged capacitors (or a bank of parallel capacitors) on separate lines to provide two separate and sequential shock pulses as controlled by the controller 74 and/or the discharge circuit 80. In some embodiments, the capacitor 78 is a relatively large capacitor for ensuring sufficient charge and decay period (i.e., long time constant and low tilt) to provide sufficient energy for shock pulses. For example, a capacitor with capacitance in the range of 200-1000 µf or more, having an associated time constant in the range of 30 ms, would typically be charged to approximately 100-200 volts and would deliver a V(peak) in a typical first waveform of about 50-100 volts leading edge. If additional shocks beyond two are administered, then a larger capacitor may be employed. In the alternative wherein the electronic package employs a circuit to further shape the waveform, the capacitor may be charged to a higher voltage range (such as around 200 V).

In one embodiment of the invention, the pulse generator includes a single capacitor 78, and the controller 74 includes a switch (e.g., a crosspoint switch) operatively associated with the capacitor 8. The controller 74 is configured to provide a shock profile consisting of a biphasic pulse (i.e., a first phase of a pulse of a predetermined polarity followed by a second phase of a pulse of reversed polarity). Monophasic and triphasic pulses may also be used. Additional shock profiles may be used having various properties including waveform, polarity, shape, periodicity, energy, voltage, etc. Exemplary shock profiles are described in U.S. Pat. No. 6,327,500 to Cooper et al., U.S. Pat. No. 5,978,705 to KenKnight et al., and U.S. Pat. No. 6,556,865 to Walcott et al., the contents of each of which are hereby incorporated by reference as if recited in full herein.

The controller 74 delivers a preselected electrical pulse to predetermined electrode pairs through a switch 82, which can be programmable. The shock generator 79 (including the capacitor charger 76, capacitor 78, and discharge circuit 80), controller 74, and switch 82 thus work in concert to produce and deliver a shock having a particular shock profile. Therefore, it will be appreciated that in operation, in response to an input from the fibrillation detector 70, the blood pressure monitor 72, and/or the shock profile selection module 110, the controller 74 controls the pulse or shock generator 79 to synchronize the delivery of the timed pulse output to the proper electrode pair in accordance with the cardiac cycle information received from the synchronization/cardiac cycle monitor 72 and the specific electrode configuration employed by or selected by the device. The electronic package may also include a receiver/transmitter coupled to the internal controller 74 for communicating with an external controller. Thus, the pulse regimen could be altered by external input to the controller to alter for example, the waveform, the voltage, the electrode coupling, or even to retrieve data monitoring data received and stored in memory about the number of atrial fibrillation episodes and the effectiveness of the shock level.

In one embodiment of the invention, the switch 82 is programmable (e.g., by remote control such as by a radio signal) to alter the coupling of the pulse generator to the shocking electrodes. This feature is advantageously employed when multiple electrodes are implanted so that the electrode pairs that deliver the shocks may be changed to optimize the technique for a particular patient.

The present invention should not be construed as limited to the configuration of FIG. 2, which is intended to encompass any configuration capable of carrying out the operations described herein.

Figure 3:
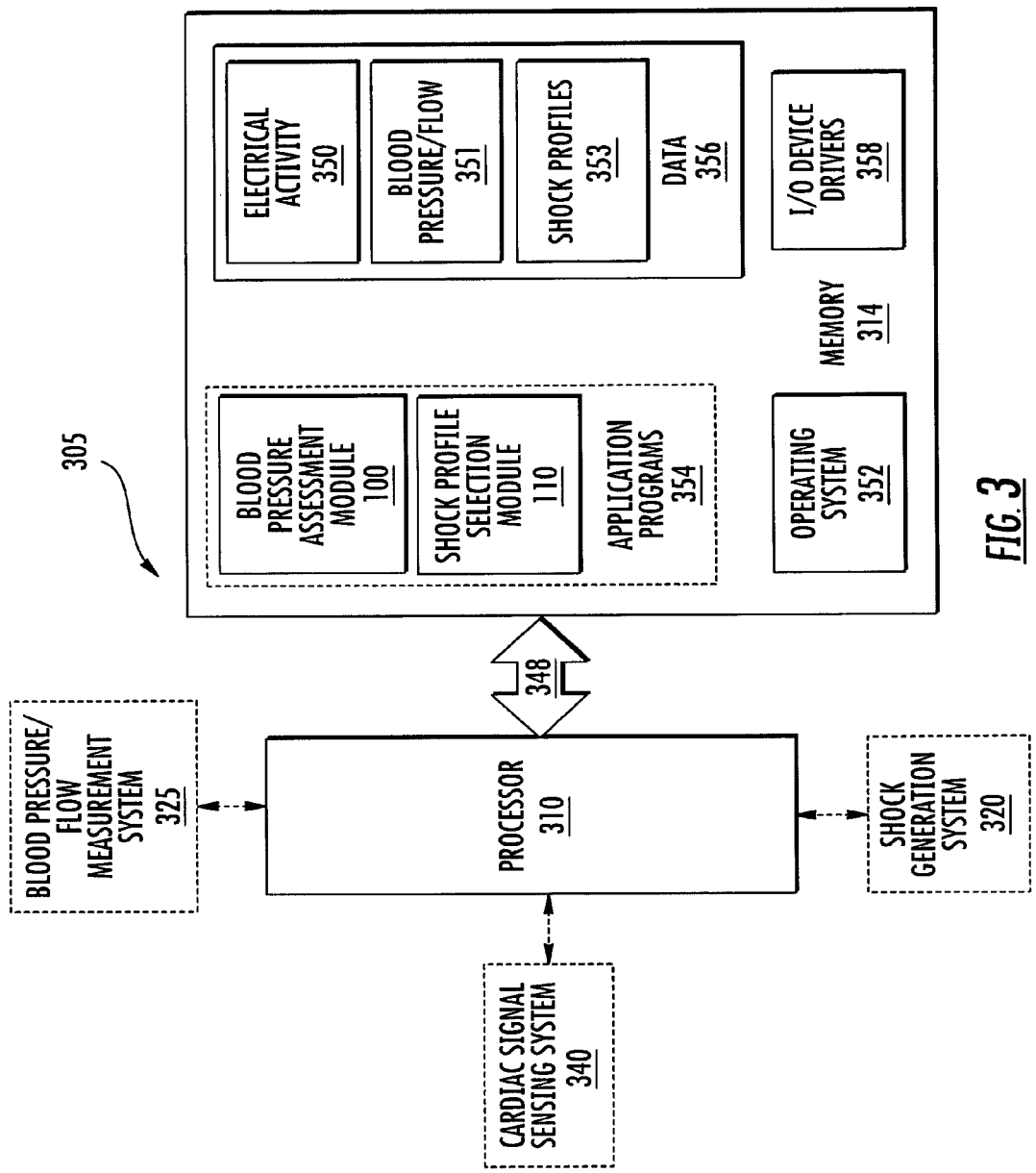
FIG. 3 is a schematic illustration of alternative embodiments of operational circuitry and/or computer program modules suitable for carrying out operations of embodiments of the present invention.

FIG. 3 is a block diagram of exemplary embodiments of data processing systems that illustrates systems, methods, and computer program products in accordance with embodiments of the present invention. As shown in FIG. 3, a data processing system 305 includes a processor 310, and is in communication with a shock generation system 320, a blood pressure measurement system 325 and a cardiac sensing system 340. Various components of the data processing system 305, the shock generation system 320, the blood pressure measurement system 325 and the cardiac sensing system 340 may be implemented externally and/or internally with respect to the patient. The shock generation system 320 and/or cardiac sensing system 340 may include overlapping elements, such as shocking and/or sensing electrodes either implanted in the patient along with the shock generation system 320 and/or cardiac sensing system 340 or situated at internal or external regions of the patient. The blood pressure measurement system 325 includes a hemodynamic sensor that detects values correlated to blood flow, and can include external and/or internal components.

The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 3, the memory 314 may include several categories of software and data used in the data processing system 305: the operating system 352; the application programs 354; the input/output (I/O) device drivers 358; a blood pressure assessment module 100; a shock profile selection module 110 and the data 356. The data 356 may include electrical activity data 350 (which can include electrical signals from the cardiac signal sensing system 340), blood pressure/flow data 351 (which may include data obtained from the blood pressure/flow measurement system) and/or shock profile data 353 (which may include a library of selectable shock profiles). The shock profile selection module 110 may communicate the shock profiles of selected shocks to a shock generation system 320 for delivery to a patient.

As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, or proprietary operating systems. The I/O device drivers 358 typically include software routines accessed through the operating system 352 by the application programs 354 to communicate with devices such as I/O data port(s), data storage 356 and certain memory 314 components and/or the shock generation system 320, blood pressure/flow measurement system 325 and cardiac signal sensing system 340. The application programs 354 are illustrative of the programs that implement the various features of the data processing system 305 and can include at least one application which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the blood pressure assessment module 100 and the shock profile selection module 110 being an application program in FIG. 3, as will be appreciated by those of skill in the art, other configurations may also be utilized while still benefiting from the teachings of the present invention. For example, the shock profile selection module 110 may also be incorporated into the operating system 352, the I/O device drivers 358 or other such logical division of the data processing system 305. Thus, the present invention should not be construed as limited to the configuration of FIG. 3, which is intended to encompass any configuration capable of carrying out the operations described herein.

In certain embodiments, the blood pressure assessment module 100 and shock profile selection module 110 includes computer program code for obtaining data associated with the blood flow of the patient, such as cardiac electrical activity data 350, blood pressure/flow data 351 and/or shock profiles 353.

The I/O data port can be used to transfer information between the data processing system 305 and the shock generation system 320, the blood pressure measurement system 325, and the cardiac signal sensing system 340 or another computer system or a network (e.g., the Internet) or to other devices controlled by the processor. These components may be conventional components such as those used in many conventional data processing systems that may be configured in accordance with the present invention to operate as described herein.

Figure 4:
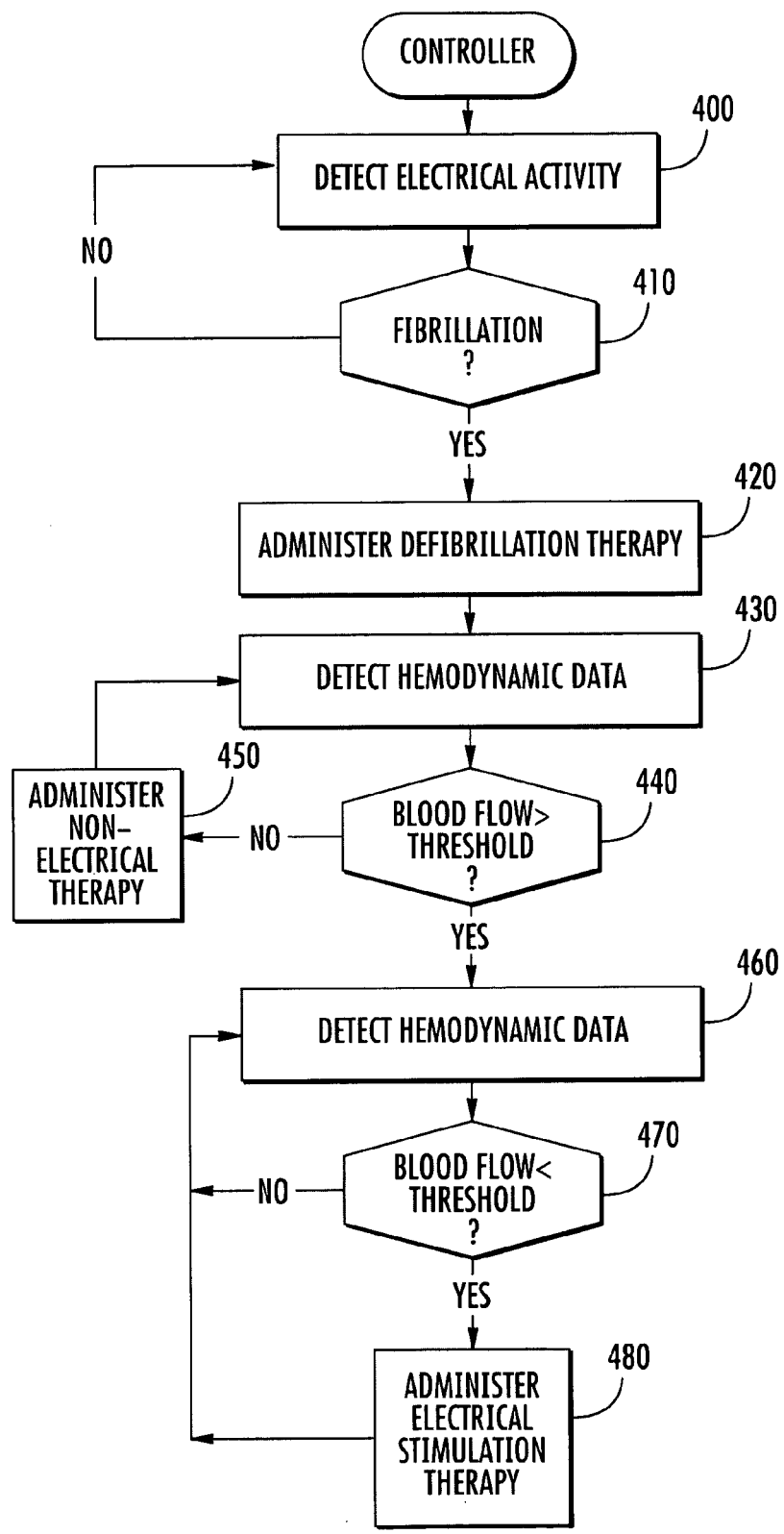
FIG. 4 is a flowchart illustrating operations that can be carried out according to embodiments of the present invention.
Figure 5:
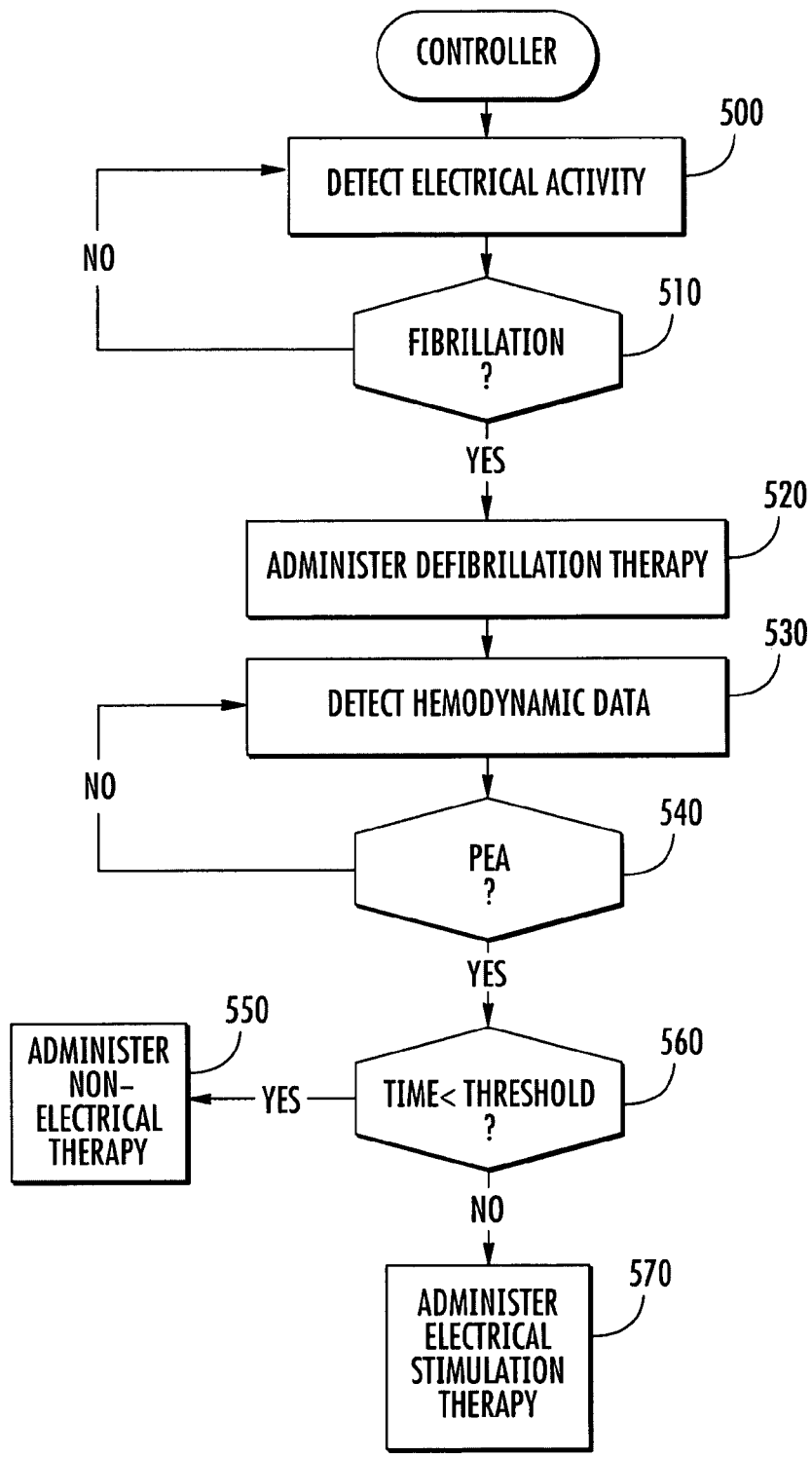
FIG. 5 is a flowchart illustrating operations according to further embodiments of the present invention.

Referring now to FIGS. 4 and 5, exemplary operations, which may be carried out by the systems depicted in FIGS. 2 and/or 3 or other suitable defibrillation system, are shown. As shown in FIG. 4, cardiac electrical activity of a subject is detected at Block 400. If fibrillation is detected at Block 410, a defibrillation therapy is administered at Block 420. The defibrillation therapy can include a defibrillation shock delivered to the heart of the subject. Hemodynamic data is detected at Block 430. If the hemodynamic data indicates that the blood flow of the subject after successful defibrillation is less than a threshold amount at Block 440 (i.e., the blood flow does not return to a normal level), then non-electrical therapy is administered in Block 450. The non-electrical therapy can include CPR, drug therapy or any therapy suitable to improve the blood flow of the subject. If the blood flow is greater than a threshold amount at Block 440, then hemodynamic data is continued to be detected at Block 460. If the blood flow is subsequently below a threshold amount at Block 470, then electrical stimulation therapy, including burst pulsing, is administered at Block 480. In some embodiments, hemodynamic data can be detected for a relatively long period of time after post-defibrillation return to normal blood flow, such as 10, 20, 30, 60 or more minutes post-defibrillation.

As shown in FIG. 5, cardiac electrical activity of a subject is detected at Block 500. If fibrillation is detected at Block 510, defibrillation therapy is administered at Block 520. Hemodynamic data is detected at Block 530. If the hemodynamic data indicates that the subject is experiencing PEA or an elevated risk of PEA at Block 540 and if the amount of time post-defibrillation is less than a threshold amount at Block 560, then non-electrical therapy is administered to increase blood flow, such as CPR and/or drug therapy. The threshold amount of time can be more than about 5-10 minutes. However, if the hemodynamic data indicates that the subject is experiencing PEA at Block 540 and if the amount of time post-defibrillation is greater than the threshold amount at Block 560, then electrical stimulation therapy is administered at Block 570.

In some embodiments, electrical therapy in Blocks 480 and 570 of FIGS. 4 and 5 may be repeated. For example, burst pulses may be automatically delivered repeatedly or burst pulses may be delivered until the blood flow is raised above an amount that indicates the risk of PEA has been reduced, such as 50 mmHg.

Although various embodiments are discussed with respect to defibrillation induced risks of PEA and/or reduced blood flow, it should be understood that non-defibrillation related reduced blood flow and/or PEA can be treated with burst pulsing as described herein according to embodiments of the current invention.

Embodiments according to the invention will now be illustrated in the following non-limiting example.

EXAMPLE

Eight pigs were studied. Defibrillation was performed following eight minutes of electrically induced ventricular fibrillation followed by cardiopulmonary resuscitation until a return of spontaneous circulation occurred. Cardiopulmonary resuscitation was stopped after the return of spontaneous circulation. If systolic blood pressure decreased to less than 50 mmHg following the return of spontaneous circulation, burst pacing was given through external defibrillation electrode pads, which were timed to occur before the T wave of the electrocardiogram so that ventricular fibrillation is not induced. A packet of 6 pulses each lasting 1 millisecond was delivered beginning 30 milliseconds after the sensed R-wave from a catheter electrode in the right ventricle. The time between the onset of successive pulses in a packet was 10 milliseconds and each pulse was a square wave having an amplitude of 10 Amps. One packet of pulses was delivered every 3 seconds. The number of packets was randomized to be 5, 10, 15, or 20 packets.

Figure 6:
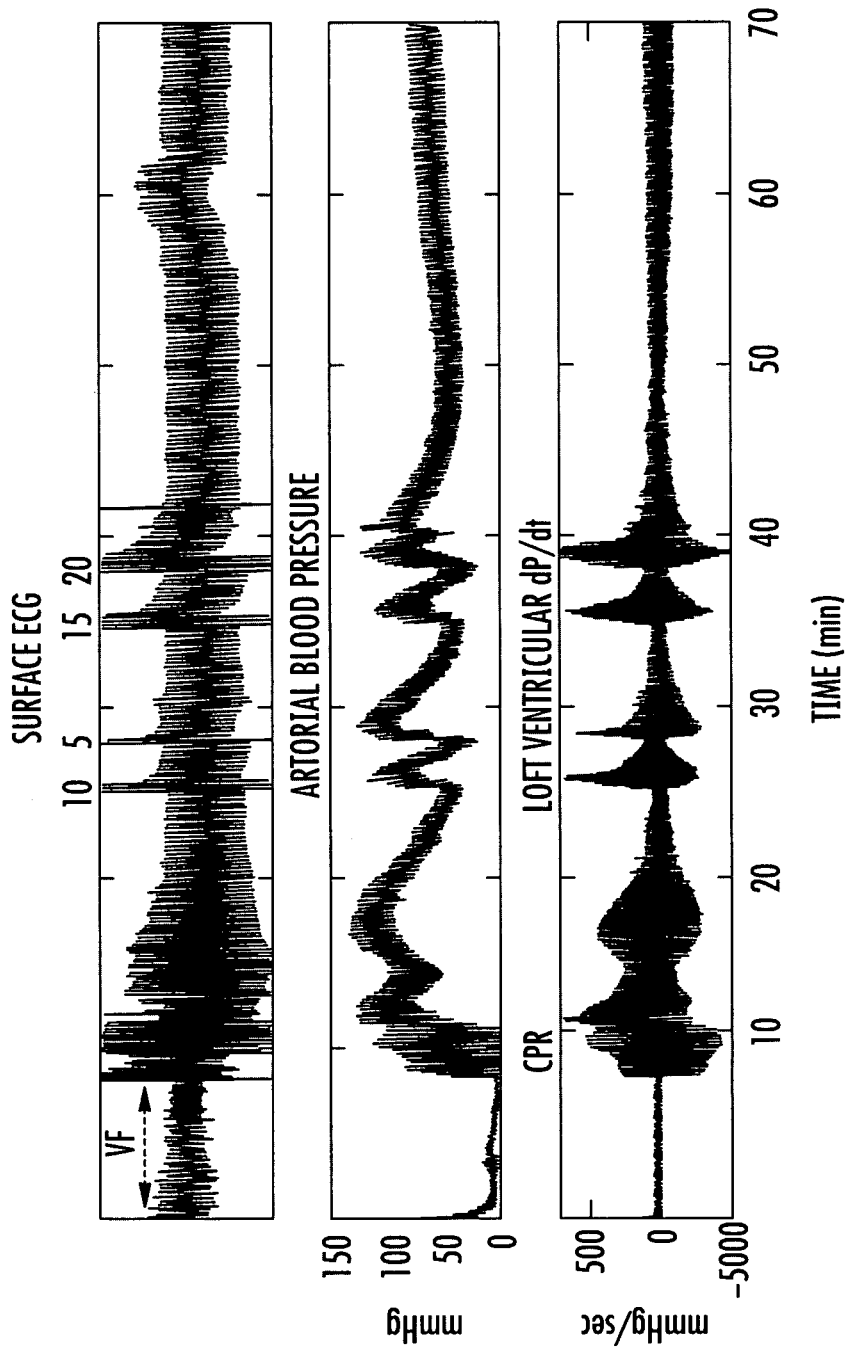
FIG. 6 are graphs of the surface ECG, the arterial blood pressure, and the left ventricular change in pressure as a function of time.

Two of the eight pigs studied never achieved the return of spontaneous circulation post-defibrillation. Two of the pigs achieved a return of spontaneous circulation post-defibrillation, which was maintained until one hour after defibrillation. Three of the pigs achieved the return of spontaneous circulation, which was followed by a subsequent blood pressure decrease to less than 50 mmHg. In these three pigs, burst pacing was immediately followed by a relatively large increase in blood pressure. No tachyphalaxis was observed; however, the burst pacing repeatedly caused a increase in blood pressure. An exemplary surface ECG, the arterial blood pressure, and the left ventricular change in pressure as a function of time are shown in FIG. 6.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of reducing a risk of pulseless electrical activity (PEA) comprising:
    monitoring a first post-defibrillation blood flow for a first time period post-defibrillation;
    administering a non-electrical therapy if the first post-defibrillation blood flow in the first time period is below a first threshold value;
    prior to administering a post-defibrillation electrical pulse therapy, detecting a second post-defibrillation blood flow of a subject in a second time period after the first time period;
    detecting a third post-defibrillation blood flow of the subject after detecting the second post-defibrillation blood flow; and
    if the second post-defibrillation blood flow of the subject is above the first threshold value and the third post-defibrillation blood flow is below a second threshold value, delivering a plurality of electrical pulses that reduces a risk of PEA, wherein the plurality of electrical pulses are between about two and six pulses with a time between pulses of between 5 and 10 ms, and the second threshold value.

2. The method of claim 1, wherein the non-electrical therapy includes a drug therapy.

3. The method of claim 1, further comprising delivering a defibrillation electrical pulse sufficient to defibrillate the heart of the subject before detecting the first post-defibrillation blood flow of the subject.

4. The method of claim 1, further comprising selecting a shock profile for the plurality of electrical pulses that is configured to reduce a likelihood of inducing fibrillation.

5. The method of claim 4, wherein the plurality of electrical pulses are delivered at a time in a cardiac electrical cycle of the heart that reduces the likelihood of inducing fibrillation.

6. The method of claim 4, wherein a magnitude of the shock profile of the plurality of electrical pulses is insufficient to induce fibrillation.

7. The method of claim 1, wherein the first threshold amount is between about 50 and 60 mmHg and the second threshold amount is between about 50 and 60 mmHg.

8. The method of claim 1, wherein each of the plurality of electrical pulses is between about one and ten amps.

9. The method of claim 1, wherein the plurality of electrical pulses is delivered at least about five minutes after the defibrillation shock.

10. The method of claim 1, further comprising repeatedly delivering the plurality of electrical pulses.

11. The method of claim 1, wherein the first threshold value is greater than about 50 mmHg and the second threshold value is less than the first threshold value.

12. A system for reducing a risk of pulseless electrical activity, the system comprising:
    a electrical pulse generator configured to deliver an electrical pulse to the heart of the subject via one or more electrodes;
    a controller configured to control the electrical pulse generator; and
    a detector configured to monitor a first post-defibrillation blood flow for a first time period post-defibrillation, to detect a second post-defibrillation blood flow of the subject that is prior to administering a post-defibrillation electrical pulse therapy, and to detect a third post-defibrillation blood flow of the subject after the second post-defibrillation blood flow, wherein the second and third post-defibrillation blood flows are detected in a second time period after the first time period;
    wherein the controller is configured to initiate administration of a non-electrical therapy if the post-defibrillation blood flow in the first time period is below a first threshold value, to deliver a plurality of electrical pulses that reduces a risk of PEA if the second post-defibrillation blood flow of the subject is above the first threshold value and the third post-defibrillation blood flow is below a second threshold value, wherein the plurality of electrical pulses are between about two and six pulses with a time between pulses of between 5 and 10 ms, and the second threshold value is less than the first threshold value.

13. The system of claim 12, wherein the controller is further configured to deliver a defibrillation electrical pulse sufficient to defibrillate the heart of the subject before delivering the plurality of electrical pulses.

14. The system of claim 12, wherein the controller is further configured to select a shock profile for the plurality of electrical pulses that is configured to reduce a likelihood of inducing fibrillation.

15. The system of claim 14, wherein the controller is configured to deliver the plurality of electrical pulses at a time in a cardiac electrical cycle of the heart that reduces the likelihood of inducing fibrillation.

16. The system of claim 14, wherein a magnitude of the shock profile of the plurality of electrical pulses is insufficient to induce fibrillation.

17. The system of claim 12, wherein the first threshold amount is between about 50 and 60 mmHg and the second threshold amount is between about 50 and 60 mmHg.

18. The system of claim 12, wherein each of the plurality of electrical pulses is between about one and ten Amps.

19. The system of claim 12, wherein the plurality of electrical pulses is administered at least about five minutes after the defibrillation shock.

20. The system of claim 12, wherein the controller is configured to repeatedly deliver the plurality of electrical pulses.

21. The system of claim 12, wherein the first threshold value is greater than about 50 mmHg and the second threshold value is less than the first threshold value.

22. A computer program product for reducing a risk of pulseless electrical activity (PEA), the computer program product comprising:
a non-transient computer readable medium having computer readable program code embodied therein, the computer readable program code comprising:
computer readable program code that monitors a first post-defibrillation blood flow for a first time period post-defibrillation;
computer readable program code that initiates administration of a non-electrical therapy if the first post-defibrillation blood flow in the first timeperiod is below a first threshold value;
computer readable program code that detects a second post-defibrillation blood flow of a subject that is prior to administering a post-defibrillation electrical pulse therapy;
computer readable program code that detects a third post-defibrillation blood flow of a subject after the first post-defibrillation blood flow, wherein the second and third post-defibrillation blood flows are detected in a second time period after the first time period;
computer readable program code that delivers a plurality of electrical pulses that reduces a likelihood of PEA if the second post-defibrillation blood flow of the subject is above the first threshold value and the third post-defibrillation blood flow is below a second threshold value, wherein the plurality of electrical pulses are between about two and six pulses with a time between pulses of between 5 and 10 ms, and the second threshold value is less than the first threshold value.

23. The computer program product of claim 22, further comprising computer readable program code that is configured to repeatedly deliver the plurality of electrical pulses.

24. The computer program product of claim 22, wherein the first threshold value is greater than about 50 mmHg and the second threshold value is less than the first threshold value.

25. A method of reducing a risk of pulseless electrical activity (PEA) comprising:
administering a non-electrical therapy if a blood flow in a first time period post-defibrillation is below about 50 mmHg;
detecting a decrease in blood flow for a heart of a subject post-defibrillation in a second time period after the return of normal systolic blood flow that is greater than about 50 mmHg; and
delivering a plurality of electrical pulses having a shock profile configured to decrease the risk of pulseless electrical activity and to reduce a likelihood of inducing fibrillation when the decrease in blood flow is detected after the return of normal blood flow that is greater than about 50 mmHg, wherein the plurality of electrical pulses are between about two and six pulses with a time between pulses of between 5 and 10 ms.

26. The method of claim 25, wherein the plurality of electrical pulses are delivered at a time in the electrical cardiac cycle to reduce the likelihood of inducing fibrillation.

27. A method of reducing a risk of pulseless electrical activity (PEA) comprising:
delivering a defibrillation electrical pulse sufficient to defibrillate a heart of a subject;
administering a non-electrical therapy if a post-defibrillation blood flow in a first time period is below about 50 mmHg;
detecting a return of normal blood flow that is greater than about 50 mmHg in a second time period that is after the first time peiod;
detecting a decrease in the blood flow of the subject after the return of normal systolic blood flow that is greater than about 50 mmHg; and
if the decrease in the blood flow is detected after a threshold time after defibrillation, administering a plurality of electrical pulses after the decrease in the blood flow is detected that reduces a risk of pulseless electrical activity, wherein the plurality of electrical pulses are between about two and six pulses with a time between pulses of between 5 and 10 ms.

* * * * *

UNITED STATES PATENT AND TRADEMARK OFFICE
CERTIFICATE OF CORRECTION

PATENT NO. : 9,101,779 B2  Page 1 of 1
APPLICATION NO. : 11/874284
DATED : August 11, 2015
INVENTOR(S) : Ideker et al.

It is certified that error appears in the above-identified patent and that said Letters Patent is hereby corrected as shown below:

In the Claims:
Column 13, Claim 22, Line 32: Please correct "timeperiod"
to read -- time period --

Signed and Sealed this
Eighth Day of March, 2016

Michelle K. Lee
*Director of the United States Patent and Trademark Office*